United States Patent [19]
Kornfeld

[11] 4,036,905
[45] July 19, 1977

[54] PROCESS FOR THE MANUFACTURE OF PROPYLENE OXIDE

[75] Inventor: Alan D. Kornfeld, East Windsor, N.J.

[73] Assignee: Oxirane Corporation, Princeton, N.J.

[21] Appl. No.: 675,864

[22] Filed: Apr. 12, 1976

[51] Int. Cl.$^2$ .............................................. C07C 1/24
[52] U.S. Cl. ...................................... 260/682; 203/9; 203/99
[58] Field of Search ....................... 260/682; 203/9, 99

[56] References Cited
U.S. PATENT DOCUMENTS

| | | | |
|---|---|---|---|
| 3,510,538 | 5/1970 | Rosenthal | 260/682 |
| 3,836,603 | 9/1974 | Connor, Jr. et al. | 260/682 |

*Primary Examiner*—C. Davis
*Attorney, Agent, or Firm*—Flynn & Frishauf

[57] ABSTRACT

In the epoxidation of propylene with tertiary butyl hydroperoxide to form propylene oxide, a by-product, tertiary butyl alcohol is formed. This alcohol can be dehydrated to form isobutylene which can be sold as a product or hydrogenated, followed by oxidation, and the resulting hydroperoxide reacted with propylene to produce propylene oxide and tertiary butyl alcohol for recycle. In this process, the operation of the tertiary butyl alcohol vaporizer is substantially improved by increasing the quantity of liquid purge to at least 15 weight percent of the input. Under such operating conditions, the organic content of the waste water effluent from the entire plant is reduced, fouling of the vaporizer heat transfer surfaces is minimized thereby increasing the on-stream time between cleanings by as much as 2-3 times the normal, and deposits are more easily removed from the vaporizer when it is shut down for cleaning.

19 Claims, 2 Drawing Figures

PROCESS FOR THE MANUFACTURE OF PROPYLENE OXIDE

FIELD OF THE INVENTION

This invention has to do with an improvement in the epoxidation of propylene oxide with tertiary butyl hydroperoxide. More specifically, it has to do with processing of a by-product stream containing tertiary butyl alcohol as a by-product and conversion of the alcohol to isobutylene.

BACKGROUND OF THE INVENTION

Pure propylene oxide is in demand for the preparation of urethane foams, for example. One of the most widespread procedures for producing propylene oxide has been the epoxidation of propylene. Typical processes are described in U.S. Pat. Nos. 3,350,422 and 3,523,956. When tertiary butyl hydroperoxide is used as the oxidizing agent, the desired propylene oxide is formed. Relatively minor quantities of acetaldehyde, propionaldehyde, acrylic aldehyde, acetone, methanol, hexenes, water, are formed, as well as tertiary butyl alcohol. Fractionation of the reaction product is required.

One of the more efficient agents for oxidizing propylene to propylene oxide is tertiary butyl hydroperoxide, because its reduction product, tertiary butyl alcohol, may be isolated and sold or recycled to reform tertiary butyl hydroperoxide by the following steps:

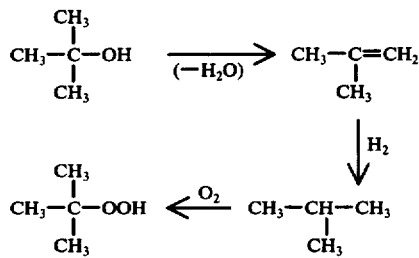

In the recovery of tertiary butyl alcohol for dehydration to isobutylene, the tertiary butyl alcohol is vaporized and this step has proven to be particularly troublesome. The crude tertiary butyl alcohol discharged as a product from the distillation of the epoxidation products contains impurities which polymerize. The polymers are deposited on heat exchange surfaces of the equipment employed to vaporize the tertiary butyl alcohol.

It is an object of the present invention to reduce the fouling of the heat transfer surface in the tertiary butyl alcohol vaporizer thereby increasing the on-stream time between cleanings.

Further, it is an object of the present invention to reduce the organic content of the waste water discharge from the propylene oxide manufacturing plant.

Another object is to soften the deposits on the heat exchanger surfaces in the tertiary butyl alcohol vaporizer so that such deposits are more easily removed.

SUMMARY OF THE INVENTION

In accordance with the present invention, there is provided a process wherein the operating conditions of the tertiary butyl alcohol vaporizer are modified whereby a substantial quantity of the crude tertiary butyl alcohol input to the vaporizer is removed as unvaporized liquid purge.

SPECIFIC EMBODIMENTS OF THE INVENTION

Vaporizer fouling is believed to be caused by polymerization of the above-mentioned impurities in the crude tertiary butyl alcohol. At the vaporizer temperatures, as from about 300° F. to about 400° F., the organic impurities adhere to the heat exchange surfaces, are decomposed and are carbonized, thereby greatly decreasing the heat transfer efficiency and obstructing the passages in the heat exchanger until eventually the process must be shut down and the heat exchanger cleaned to remove all accumulated deposits.

In accordance with the present invention, the deposits on the heat exchanger surfaces of the vaporizer are reduced by altering the process conditions so that a maximum of about 85 weight percent of the tertiary butyl alcohol fed to the vaporizer is vaporized, and at least about 15, and preferably from about 20 to about 40, weight percent of the tertiary butyl alcohol is blown down (removed as a bottoms fraction from the vaporizer). More preferably, the vaporizer is operated so that from about 70 to about 80 weight percent of a crude tertiary butyl alcohol feed stock passes to the dehydration reactor and about 20 to about 30 weight percent of the feed stock is so blown down.

Table I gives the results of an analysis of the total effluent from a propylene oxide manufacturing plant under various conditions of operating the tertiary butyl alcohol vaporizer. The operating time between vaporizer shutdown and the character of the deposits built up within the vaporizer are also summarized in Table I.

TABLE I

| Unvaporized Liquid Purge (Wt. %) | Total Tons Vaporized | Total Organic Content, in population equivalents,* of Plant Effluent (in stream 25) | Nature of Deposit On Heat Exchanger Surface |
|---|---|---|---|
| 8 | 40,000 | 4625 | Hard |
| 20 | 62,000 | 3125 | Soft and Easily Removed |
| 25 | 80,000 | 2500 | Soft and Easily Removed |

*Population equivalent = 180 grams of carbon oxygen demand (COD) per day

The organic content of the plant effluent slowly decreases as the material blown down from the vaporizer is increased up to about 40 weight percent of the vaporizer input. Although a smaller weight percent of tertiary butyl alcohol is vaporized and passes to the dehydration reactor under the preferred operating conditions (20–30 weight percent unvaporized liquid purge), this can be compensated for by increasing the feed rate of the crude tertiary butyl alcohol to the vaporizer.

For a better understanding of the present invention, a discussion of the various process steps will be given in conjunction with the figures.

Figure 1:
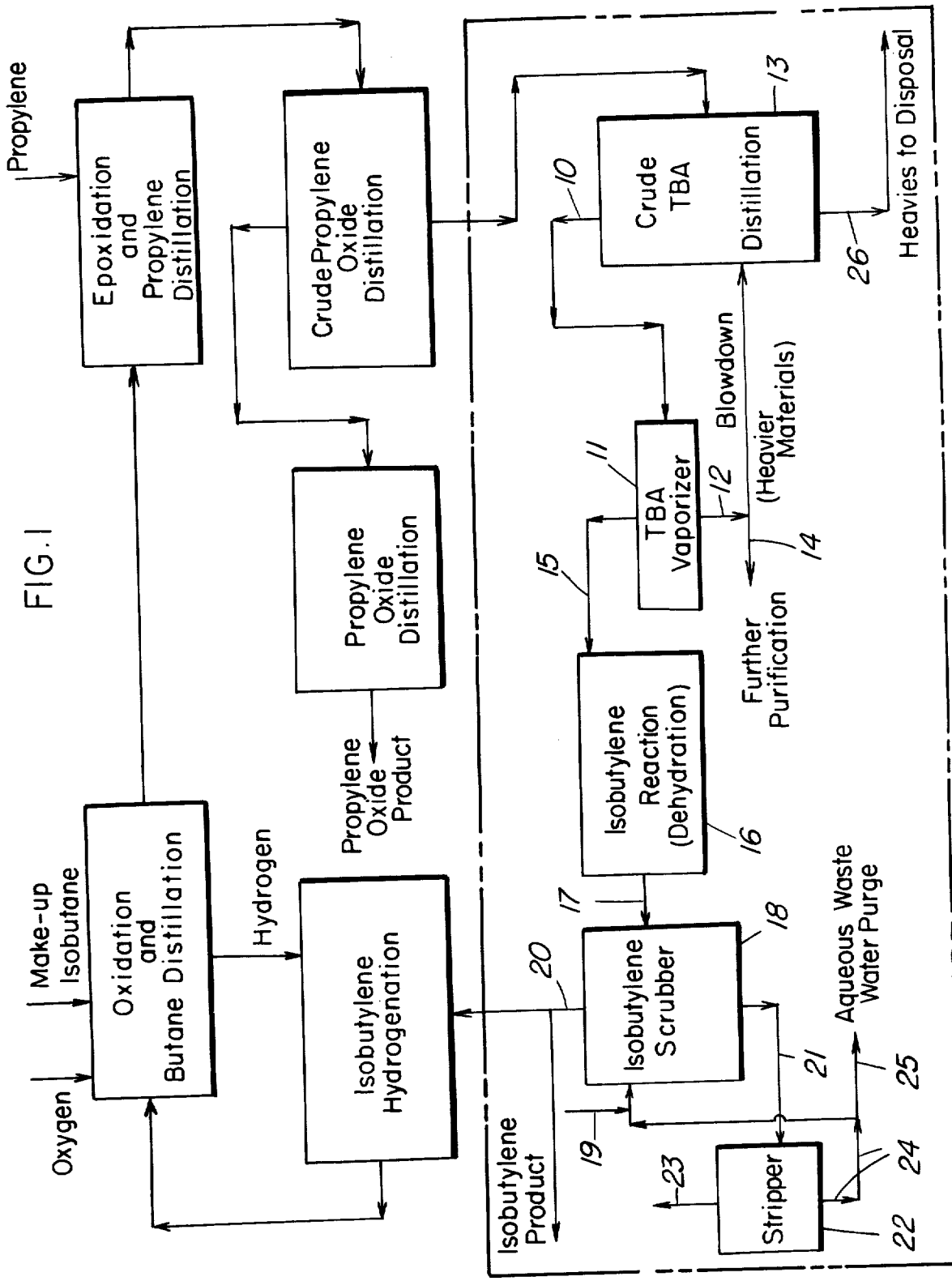
FIG. 1 is a flow diagram of propylene oxide manufacturing process including the isolation and recycling of tertiary butyl alcohol to form tertiary butyl hydroperoxide.

The process broadly shown in FIG. 1, and the operating parameters of that process, are described in detail in U.S. Pat. Nos. 3,351,635 and 3,523,956, the disclosures of which patents are incorporated herein by reference.

Figure 2:
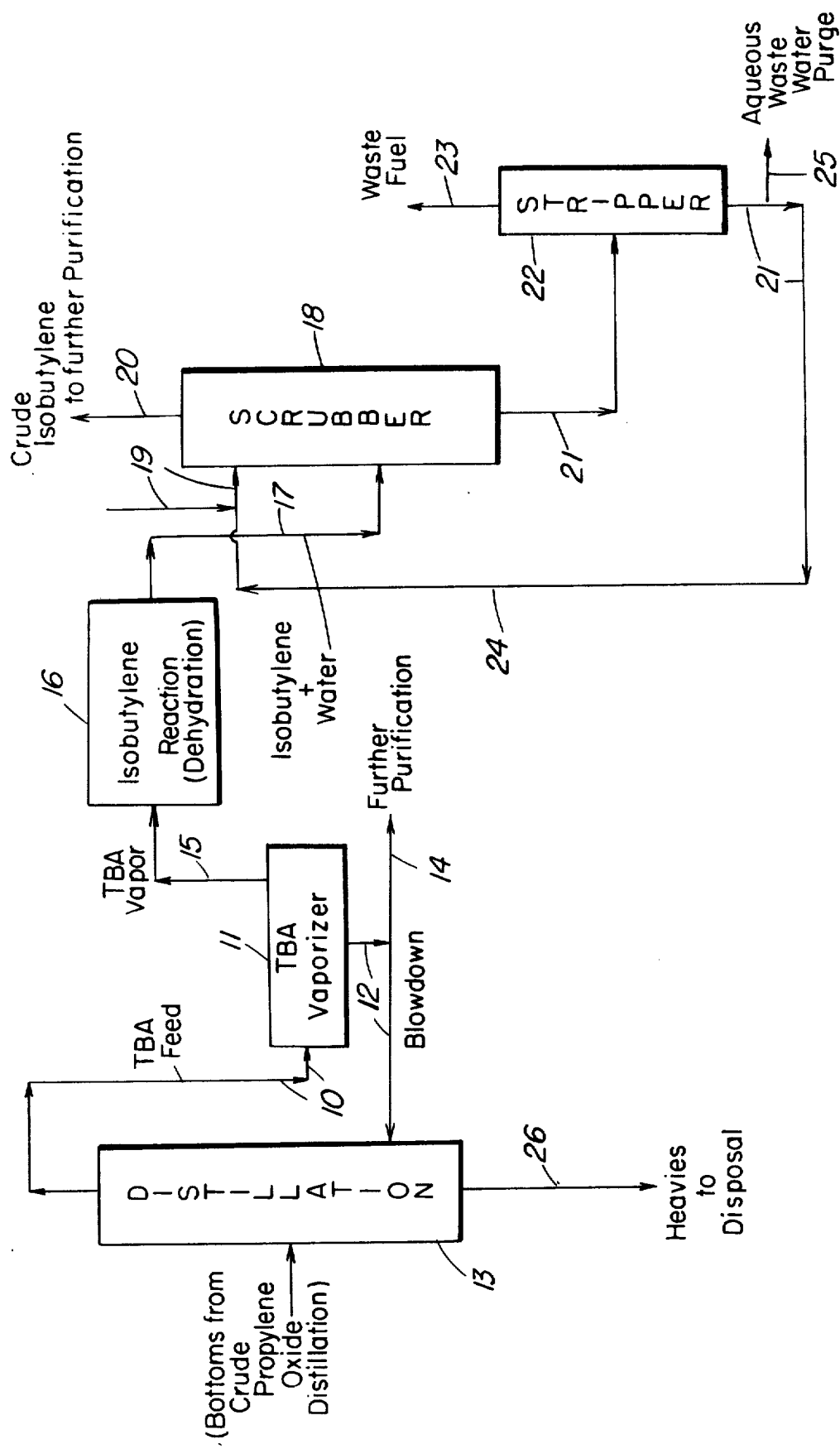
FIG. 2 is a flow diagram of the process of the present invention.

The area of the present invention is that portion of FIG. 1 which is enclosed in dotted lines and is reproduced in FIG. 2.

In FIG. 2, a feed stream 10 containing tertiary butyl alcohol, particularly a crude tertiary butyl alcohol containing impurities identified above, at temperatures between 75° F. and 200° F., is introduced into a vaporizer 11 under controlled conditions whereby at least 15% and not more than about 40% of the feed is blown down through line 12 to the still 13 or to further purification via line 14. The vaporizer is operated at temperatures between about 300° F. and about 500° F., and preferably between 325° F. and 400° F. The tertiary butyl alcohol that is vaporized at temperatures between 325° F. and 400° F. is passed through conduit 15 into one or more dehydration reactors 16. The dehydration reactor catalyst can be a porous form of aluminum oxide of high surface area such as Alcoa's F-1, Activated Alumina, as shown and described in U.S. Pat. No. 3,665,048. The quantity of catalyst required is related to the temperature and feed rates at which the reaction occurs. Normally, between 0.5 and 10 parts by weight of alcohol are fed per hour per part by weight of catalyst. Preferably, the feed rate is such that 2 to 4 parts by weight of alcohol per hour are introduced to reactor 16 per part by weight of catalyst. The temperature within reactor 16 is maintained between 475° F. and 775° F. The pressure at which the reaction takes place is not critical and satisfactory results are obtained in the range between atmospheric pressure and 300 p.s.i.g. For ease in downstream separation of the isobutylene from other reaction products, it is preferred to operate reactor 16 with an inlet pressure of about 100 to 250 p.s.i.g.

The effluent from reactor 16 passes through line 17 into a caustic water scrubber column 18, wherein the crude isobutylene is separated from acidic compounds by action of caustic water passed to scrubber 18 through line 19. The caustic water generally contains less than about 5 weight percent (e.g. about 0.1%) of NaOH. Crude isobutylene from scrubber 18 passes overhead through conduit 20 to further distillation columns (not shown) wherein the isobutylene is further purified as required. The isobutylene is either sold or is recycled to form tertiary butyl hydroperoxide by the process discussed above, involving hydrogenation to isobutane followed by oxidation; this is illustrated by suitable process blocks in FIG. 1. Used caustic water stream 21 is passed to stripper 22 where light impurities are removed overhead through line 23. The bottom water-caustic stream 24 is recycled to column 18 via line 19 with a portion being purged via line 25. Overhead 23 from stripper 22 can be used as fuel.

Returning to distillation column 14, heavy materials are removed as a bottoms product through line 26 for disposal from the system.

FIG. 1 and the above discussion are exemplary of the major process equipment necessary for dehydrating tertiary butyl alcohol derived from the epoxidation of propylene with tertiary butyl hydroperoxide using the present disclosure. There are many valves and heat exchangers that are included in the process to increase efficiency of over-all operation. However, these are conventional and within the purview of those skilled in the art.

The advantages of the present invention are most apparent from the following examples which show by way of comparison the improvement resulting from increasing the quantity of non-volatile liquid purge from the vaporizer.

EXAMPLE I (COMPARATIVE)

A stream of tertiary butyl alcohol (TBA) from still 13 containing 96 weight percent TBA and 4 weight percent of other material is fed to vaporizer 11. The vaporizer is operated at temperatures between 355° F. and 365° F. and at pressures varying from 207 p.s.i.g. to 223 p.s.i.g. About 8% of the feed stream is returned as a liquid purge to still 13 and about 92% of the feed stream is vaporized, heated and sent to the dehydration reactors 16 which are operated between 700° F. and 750° F. The liquid purge from stripper 22 contained 4625 population equivalents of organic wastes that were purged during this period. About 40,000 tons of feed were sent to vaporizer 11 prior to having to stop operation to clean the vaporizer due to a reduction in heat transfer. The polymeric foulant on the vaporizer tubes was a hard black material that was difficult to remove.

EXAMPLE II

The purity of the feed TBA stream to the vaporizer was the same as in Example I and the vaporizer was operated over the same temperature and pressure range. However, the average liquid returned to distillation still 13 was 20% of the feed stream. Dehydration reactor conditions were maintained similar to those of Example I. The organic content of the purge liquid stream from stripper 22 was found to be 3125 population equivalents as an average during this operation. About 62,000 tons of feed were sent to vaporizer 11 prior to having to stop in order to clean this unit. The nature of the foulant on the tubes of the vaporizer was found to be a softer, more easily removed material than the polymeric material found in Example I.

What is claimed is:

1. In a process for the production of isobutylene from tertiary butyl alcohol wherein a mixture containing tertiary butyl alcohol is fractionated in a fractionator, the tertiary butyl alcohol so fractionated is vaporized and a fraction containing less volatile impurities is separated from the vaporized tertiary butyl alcohol and is recycled to said fractionator, the vaporized tertiary butyl alcohol is dehydrated in dehydration zone to form isobutylene, the isobutylene is contacted with an aqueous alkali, and an aqueous waste stream is formed, the improvement which comprises vaporizing up to a maximum of about 85 percent by weight of said fractionated tertiary butyl alcohol and passing said vaporized tertiary butyl alcohol to said dehydration zone.

2. The process of claim 1, wherein said fraction comprises at least about 15 weight percent.

3. The process of claim 1, wherein from about 60 to about 80 weight percent of said fractionated tertiary butyl alcohol is vaporized and so passed to said dehydration zone, and said fraction comprises from about 40 to about 20 weight percent.

4. The process of claim 1, wherein from about 70 to about 80 weight percent of said fractionated tertiary butyl alcohol is vaporized and so passed to said dehydration zone, and said fraction comprises from about 40 to about 20 weight percent.

5. In a continuous process for the production of isobutylene from a feed stock containing tertiary butyl alcohol and polymerizable impurities, wherein the feed stock is passed from a fractionation column into a vaporizer to vaporize tertiary butyl alcohol and to remove therefrom a fraction containing less volatile impurities, a major portion of the vaporized tertiary butyl alcohol from said vaporizer is converted to isobutylene in a dehydration zone, and the less volatile impurities from said vaporizer are returned to said fractionation column and removed for further purification; the improvement which comprises operating the vaporizer so that a maximum of about 85 weight percent of the feed stock charged thereto flows to the dehydration zone and is converted to isobutylene, and at least about 15 weight percent of the feed stock charged thereto is recycled to said fractionation column and removed for further purification.

6. The process of claim 5, wherein the vaporizer is so operated that from about 60 to about 80 weight percent of the feed stock charged thereto flows to the dehydration zone, and from about 40 to about 20 weight percent of the feed stock charged thereto is recycled to said fractionating column.

7. The process of claim 5, wherein the vaporizer is so operated that from about 70 to about 80 weight percent of the feed stock charged thereto flows to the dehydration zone, and from about 30 to about 20 weight percent of the feed stock charged thereto is recycled to said fractionating column.

8. The process of claim 5, wherein the dehydration zone is maintained at a temperature of between about 475° F. and about 775° F.

9. The process of claim 5, wherein the said feed stock is at a temperature of between about 75° F. and about 200° F.

10. The process of claim 5, wherein the vaporizer is operated at a temperature of from about 300° F. to about 500° F.

11. The process of claim 5, wherein said feed stock contains at least about 90 weight percent of tertiary butyl alcohol and up to about 10 weight percent of impurities.

12. In a continuous process for the production of isobutylene from a feed stock containing tertiary butyl alcohol and polymerizable impurities, wherein the feed stock is passed from a fractionation column into a vaporizer to separate tertiary butyl alcohol from less volatile impurities, the volatile tertiary butyl alcohol from said vaporizer is converted to isobutylene in a dehydration zone and the less volatile impurities from said vaporizer are returned to said fractionation column, the improvement which comprises maintaining the vaporizer at a temperature in the range of from about 325° F. to about 400° F., volatilizing from about 70 weight percent to about 80 weight percent of the feed stock, converting said volatilized feed stock to isobutylene in a dehydration zone and removing at bottoms product from the vaporizer comprising about 20 weight percent to about 30 percent of the feed stock and passing said bottoms product to said fractionation column.

13. In a continuous process for the production of isobutylene from a feed stock containing tertiary butyl alcohol and polymerizable impurities, wherein the feed stock is passed from a fractionation column into a vaporizer to vaporize tertiary butyl alcohol and to remove therefrom a fraction containing less volatile impurities, a major portion of the vaporized tertiary butyl alcohol from said vaporizer is converted to isobutylene in a dehydration zone, and the less volatile impurities from said vaporizer are returned to said fractionation column or removed for further purification; the improvement which comprises operating the vaporizer so that a maximum of about 85 weight percent of the feed stock charged thereto flows to the dehydration zone and is converted to isobutylene, and at least about 15 weight percent of the feed stock charged thereto is recycled to said fractionation column or removed for further purification.

14. The process of claim 13, wherein the vaporizer is so operated that from about 60 to about 80 weight percent of the feed stock charged thereto flows to the dehydration zone, and from about 40 to about 20 weight percent of the feed stock charged thereto is recycled to said fractionation column.

15. The process of claim 13, wherein the vaporizer is so operated that from about 70 to about 80 weight percent of the feed stock charged thereto flows to the dehydration zone, and from about 30 to about 20 weight percent of the feed stock charged thereto is recycled to said fractionating column.

16. The process of claim 13, wherein the dehydration zone is maintained at a temperature of between about 475° F. and about 775° F.

17. The process of claim 13, wherein the said feed stock is at a temperature of between about 75° F. and about 200° F.

18. The process of claim 13, wherein the vaporizer is operated at a temperature of from about 300° F. to about 500° F.

19. The process of claim 13, wherein said feed stock contains at least about 90 weight percent of tertiary butyl alcohol and up to about 10 weight percent of impurities.

* * * * *